US00PP36945P2

(12) United States Plant Patent
Schoone

(10) Patent No.: US PP36,945 P2
(45) Date of Patent: Sep. 9, 2025

(54) ***PHALAENOPSIS* PLANT NAMED 'Bombshell'**

(50) Latin Name: *Phalaenopsis hybrida*
Varietal Denomination: Bombshell

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 19/171,325

(22) Filed: Apr. 6, 2025

Related U.S. Application Data

(60) Provisional application No. 63/575,712, filed on Apr. 6, 2024.

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Phalaenopsis* plant named 'Bombshell', characterized by its upright plant habit; strong flowering stems; narrow, healthy and sturdy leaves; freely flowering habit with typically two inflorescences developing per plant, each inflorescence with numerous flowers; light purple-colored flowers with mostly white and yellow-colored labella; and good postproduction longevity.

2 Drawing Sheets

Figure 1:
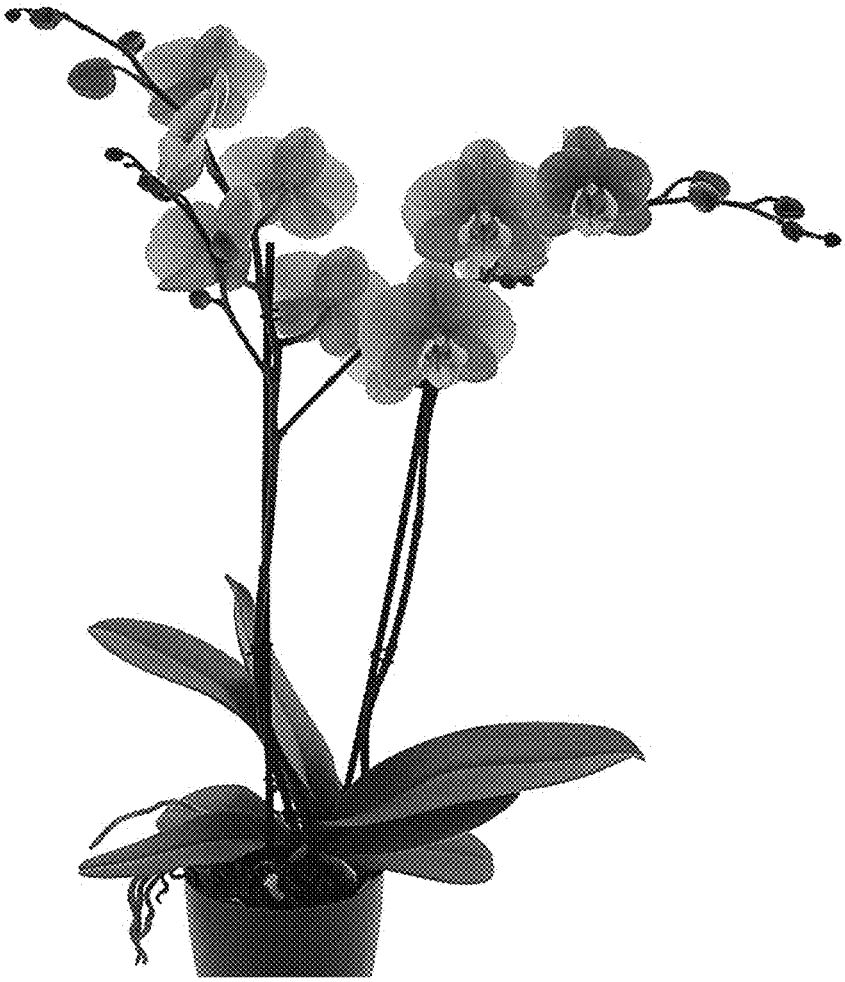

Botanical designation: *Phalaenopsis hybrida.*
Cultivar denomination: 'BOMBSHELL'.

CROSS-REFERENCED TO CLOSELY-RELATED APPLICATIONS

Title: Varieties of *Phalaenopsis* Plants
Inventor: René Schoone
Filed: Apr. 6, 2024
Ser. No. 63/575,712

Inventor and Applicant/Assignee hereby claims the benefit of this provisional U.S. Patent Application.

A European Community Plant Breeder's Rights application for the instant plant was filed by the Applicant/Assignee, Floricultura B.V. of Heemskerk, The Netherlands on Jun. 7, 2024, application number 2024/1298. Foreign priority is not claimed to this application.

BACKGROUND OF THE INVENTION

The present invention relates to a new and distinct cultivar of *Phalaenopsis* plant, botanically known as *Phalaenopsis hybrida*, and hereinafter referred to by the name 'Bombshell'.

The new *Phalaenopsis* plant is a product of a planned breeding program conducted by the Inventor in Assendelft and Heemskerk, The Netherlands. The objective of the breeding program is to develop new fast-growing and freely flowering *Phalaenopsis* plants with good leaf shape and flowers with unique and attractive patterns and coloration.

The new *Phalaenopsis* plant originated from a cross-pollination in May 2014 in Assendelft, The Netherlands of *Phalaenopsis hybrida* 'Chiada Jill', not patented, as the female, or seed, parent with an unnamed proprietary selection derived from the crossing of *Phalaenopsis hybrida*

'Schilleriana' X 'Malibu', not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in July 2020.

Asexual reproduction of the new *Phalaenopsis* plant by in vitro meristem propagation in a controlled environment in Assendelft, The Netherlands since June 2021 has shown that the unique features of this new *Phalaenopsis* plant are stable and reproduced true to type in successive generations.

SUMMARY OF THE INVENTION

Plants of the new *Phalaenopsis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Bombshell'. These characteristics in combination distinguish 'Bombshell' as a new and distinct *Phalaenopsis* plant:

1. Upright plant habit.
2. Strong flowering stems.
3. Narrow, healthy and sturdy leaves.
4. Freely flowering habit with typically two inflorescences developing per plant, each inflorescence with numerous flowers.
5. Light purple-colored flowers with mostly white and yellow-colored labella.
6. Good postproduction longevity.

Plants of the new *Phalaenopsis* can be compared to plants of the female parent, 'Chiada Jill'. Plants of the new

*Phalaenopsis* differ primarily from plants of 'Chiada Jill' in labella coloration as the lateral lobes of the labella of plants of the new *Phalaenopsis* are mostly white and yellow in color whereas the lateral lobes of the labella of plants of 'Chiada Jill' are a mix of orange, yellow and violet in color. In addition, the central lobe of the labella of plants of the new *Phalaenopsis* is mostly white in color whereas the central lobes of the labella of plants of 'Chiada Jill' are a mix of orange, yellow, white and violet in color.

Plants of the new *Phalaenopsis* can be compared to plants of the male parent selection. Plants of the new *Phalaenopsis* differ primarily from plants of the male parent selection in labella shape as the central lobe of the labella of plants of the new *Phalaenopsis* is separate from the lateral lobes and is ovate-rhomboidal to deltoid in shape whereas the central lobes of the labella of plants of the male parent selection are fused with the lateral lobes forming a "big lip" shape.

Plants of the new *Phalaenopsis* can be compared to plants of *Phalaenopsis hybrida* 'Cover Girl', not patented. In side-by-side comparisons, plants of the new *Phalaenopsis* differ primarily from plants of 'Cover Girl' in labella shape as the central lobe of the labella of plants of the new *Phalaenopsis* is ovate-rhomboidal to deltoid in shape whereas the central lobes of the labella of plants of 'Cover Girl' are ovate in shape. In addition, the column of flowers of plants of the new *Phalaenopsis* are mostly pale purple in color whereas the columns of flowers of 'Cover Girl' are white in color.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'Bombshell' grown in a container.

Figure 2:
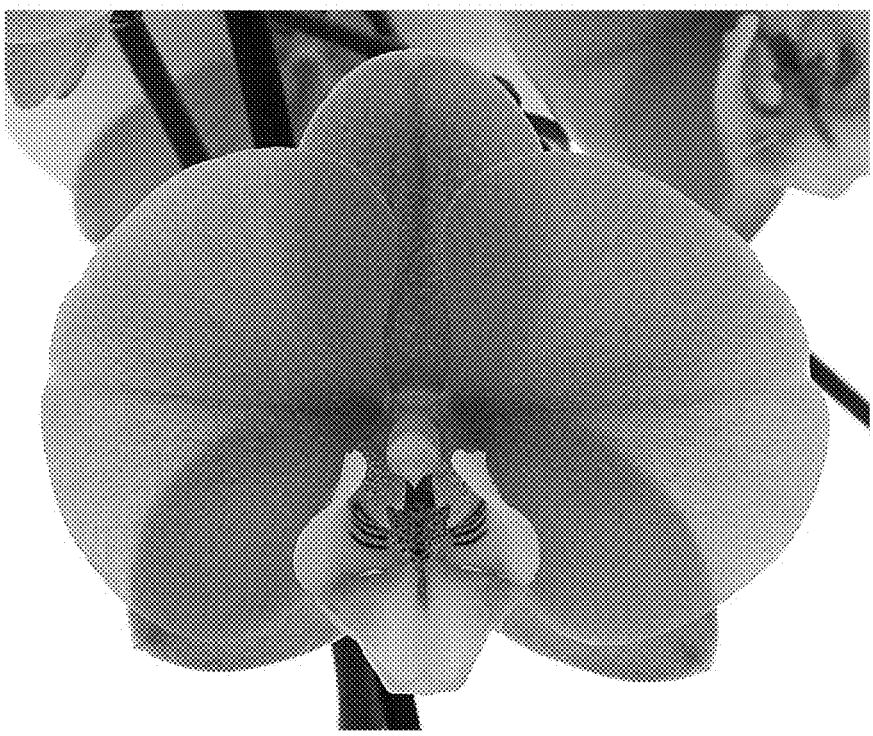

The photograph on the second sheet (FIG. 2) is a close-up view of a typical flower of 'Bombshell'.

DETAILED BOTANICAL DESCRIPTION

The aforementioned photographs and following observations and measurements describe plants grown during the late summer in 11-cm containers in a glass-covered greenhouse in Heemskerk, The Netherlands and under cultural practices typically used in commercial *Phalaenopsis* production. Plants were 18 months old when the photographs and description were taken. During the first twelve months of production of the plants, day and night temperatures averaged 27° C. During the final months of production of the plants, day temperatures ranged from 20° C. to 22° C. and night temperatures ranged from 18° C. to 20° C. During the production of the plants, light levels ranged from a minimum of 5 klux to a maximum of 10 klux. In the following description, color references are made to The Royal Horticultural Society Colour Chart, 2015 Edition, except where general terms of ordinary dictionary significance are used.

Botanical classification: *Phalaenopsis hybrida* 'Bombshell'.

Parentage:

*Female, or seed, parent.*—*Phalaenopsis hybrida* 'Chiada Jill', not patented.

*Male, or pollen, parent.*—Unnamed proprietary selection derived from the crossing of *Phalaenopsis hybrida* 'Schilleriana' X 'Malibu', not patented.

Propagation:

*Type.*—By in vitro meristem propagation.

*Time to initiate roots, summer and winter.*—About two weeks at temperatures about 28° C. to 30° C.

*Time to produce a rooted young plant, summer and winter.*—About 20 to 25 weeks at temperatures about 28° C. to 30° C.

*Root description.*—Thin, fibrous; typically light yellowish white in color; actual color of the roots is dependent on substrate composition, water quality, fertilizer, substrate temperature and age of roots.

*Rooting habit.*—Freely branching; medium density.

Plant description:

*Plant form and growth habit.*—Herbaceous epiphyte; upright plant habit with typically two inflorescences developing per plant, each inflorescence with numerous flowers; monopodial; moderately vigorous growth habit and moderate growth rate.

*Plant height, substrate level to top of foliar plane.*—About 12.2 cm.

*Plant height, substrate level to top of floral plane.*—About 50.6 cm.

*Plant diameter or spread.*—About 35.4 cm.

Leaf description:

*Arrangement and quantity.*—Distichous, simple; sessile; about six to seven fully-developed leaves per plant.

*Length.*—About 21.9 cm.

*Width.*—About 7.5 cm.

*Aspect.*—Horizontal to semi-erect.

*Shape.*—Obovate-oblong to narrowly obovate-oblong; slightly carinate.

*Apex.*—Unequal obtuse to broadly unequal acute.

*Base.*—Sheathing. Sheath length: About 1.7 cm. Sheath width: About 1.4 cm. Sheath color, upper and lower surfaces: Close to 146C; towards the margins, strongly tinged with close to N200B.

*Margin.*—Entire.

*Texture and luster, upper surface.*—Smooth, glabrous; slightly glossy.

*Texture and luster, lower surface.*—Smooth, glabrous; moderately glossy.

*Venation pattern.*—Camptodromous.

*Color.*—Developing leaves, upper surface: Close to NN137B; narrow marginal edges, close to N200A. Developing leaves, lower surface: Close to 146B strongly tinged with close to N186C; narrow marginal edges, close to a blend of N186C and N200A. Fully expanded leaves, upper surface: Close to a blend of 144A and 146A; narrow marginal edges, close to 152A; venation, close to 148A. Fully expanded leaves, lower surface: Close to 146B and 146C slightly tinged with close to N186C; narrow marginal edges, close to N199A; venation, close to 146A.

Inflorescence description:

*Appearance and flowering habit.*—Showy zygomorphic flowers arranged on axillary simple or branched racemes; typically two inflorescences develop per plant; each inflorescence with about 16 flowers; flowers face mostly outwardly on outwardly arching inflorescences supported by upright peduncles; flowers with three petals, two lateral petals and one center petal transformed into a labellum and three sepals.

*Fragrance*.—None detected.

*Time to flower*.—Plants begin flowering about six months after planting; plants flower naturally during the winter into the spring.

*Flower longevity and postproduction longevity*.—Long flowering period and good postproduction longevity, individual flowers maintain good substance for about seven weeks on the plant; flowers not persistent.

*Inflorescence length* (*lowermost flower to inflorescence apex*).—About 32.1 cm.

*Inflorescence width*.—About 21.6 cm.

*Flower buds*.—Height: About 2 cm. Diameter: About 1.4 cm by 1.7 cm. Shape: Broadly ovate. Color: Close to 177D strongly tinged with close to N77B.

*Flower size*.—About 7 cm (vertical) by 8.7 cm (horizontal).

*Flower depth*.—About 2.9 cm.

*Petals, quantity and arrangement*.—Three, two lateral petals and one center petal transformed into a labellum.

*Lateral petals*.—Length: About 4.2 cm. Width: About 5.5 cm. Shape: Broadly reniform; not fused. Apex: Broadly obtuse and shallowly retuse. Margin: Entire. Texture and luster, upper and lower surfaces: Smooth, glabrous; moderately velvety; matte. Color: When opening, upper surface: Close to NN78A; towards the margins and apex, close to N75A; at the base, fine dots, close to 76A. When opening, lower surface: Close to N75D; fading towards the center to close to 84D; at the base, close to N78C. Fully opened, upper surface: Close to NN78B; towards the margins and apex, close to N75B and N75C; lower half of petal fading to close to a blend of 76B and 84C; at the base, fine dots, close to 76B; color does not change with subsequent development. Fully opened, lower surface: Close to 76A; fading towards the center to close to 84C; at the base, close to N78D; color does not change with subsequent development.

*Labella*.—Appearance: Three-parted with two lateral lobes and a central lobe. Length, lateral lobes: About 2.2 cm. Width, lateral lobes: About 1.7 cm. Length, central lobe: About 2.2 cm. Width, central lobe: About 0.8 cm to 2.5 cm. Shape, lateral lobes: Obovate; moderately curved. Shape, central lobe: Ovate-rhomboidal to deltoid with an elongated apex. Apex, lateral lobes: Obtuse. Apex, central lobe: Bluntly acute with two cirrhose apices curled upwards and backwards. Margins, lateral and central lobes: Entire. Texture and luster, lateral and central lobes, upper and lower surfaces: Smooth, glabrous, velvety; matte. Callosities: Located at the base of the labellum and attachment point of the lateral petals; about 5 mm in length, about 7 mm in width and about 6 mm in height. Color, lateral lobes: When opening, upper surface: Close to NN155D; lower marginal edges, close to 3C; at the base, axial stripes, close to 187B to 187D. When opening, lower surface: Close to NN155D; lower marginal edges, close to 2B and 2C. Fully opened, upper surface: Close to NN155D; lower marginal edges, close to 7D; at the base, axial stripes, close to 187B to 187D. Fully opened, lower surface: Close to NN155D; lower marginal edges, close to 8B. Color, central lobe: When opening, upper surface: Close to NN155D; towards the base, close to 3C and 3D; upper margin and main vein with fine dots, close to 184A to 184C; at the base, close to 155A and N78C to N78D with radial stripes, close to 184A and 184B; cirrhose apices, close to NN155D. When opening, lower surface: Close to NN155D; towards the base, close to 2C and 2D; upper margin strongly tinged with close to 166C and 166D; at the base, close to 76C and N78B; cirrhose apices, close to NN155D. Fully opened, upper surface: Close to NN155D; towards the base, close to 6D; upper margin and main vein with blotch, close to 182A and 182B; at the base, close to 10C and N78C to N78D with radial stripes, close to 184A and 184B; cirrhose apices, close to NN155D. Fully opened, lower surface: Close to NN155D; towards the base, close to 2C and 2D; upper margin with blotch, close to 174B; at the base, close to 76B and N78B; cirrhose apices, close to NN155D. Color, callosities: When developing: Close to 155A; towards the apex, close to 12A; densely dotted and blotched with close to 185A. Fully developed: Close to 2D; towards the apex, close to 13B; densely dotted and blotched with close to 185A.

*Sepals*.—Quantity and arrangement: Three, one upper dorsal sepal and two lower lateral sepals. Length, dorsal sepal: About 4.1 cm. Width, dorsal sepal: About 3.2 cm. Length, lateral sepals: About 4.4 cm. Width, lateral sepals: About 3 cm. Shape, dorsal sepal: Obovate to elliptic. Shape, lateral sepals: Ovate. Apex, dorsal sepal: Obtuse with a minute acute tip. Apex, lateral sepals: Broadly acute. Base, dorsal and lateral sepals: Cuneate. Margins, dorsal and lateral sepals: Entire. Texture and luster, dorsal and lateral sepals, upper and lower surfaces: Smooth, glabrous; moderately velvety; matte. Color, dorsal sepal: When opening, upper surface: Close to N78B; towards the margins and apex, close to 76A; fine dots, close to 76C and 76D; main vein, close to N78B and N78C. When opening, lower surface: Close to a blend of 70B and 70C; broad marginal edges, close to N75C; main vein, close to 185B. Fully opened, upper surface: Close to NN78B; towards the margins and apex, close to N75D; fine dots, close to 76A. Fully opened, lower surface: Close to N75A; towards the base, close to N75C and N75D; broad marginal edges, close to 76A; main vein, close to 77B and 77C. Color, lateral sepals: When opening, upper surface: Close to 76B and 76C; towards the base, close to N78B and fading to close to 77C; basal blotch, close to 150D; fine dots, close to N78A. When opening, lower surface: Close to N78C; lower half tinged with close to 195B; venation, close to 183C. Fully opened, upper surface: Close to 76B; towards the base, close to N78B and N78C; basal blotch, close to 157C and 157D; fine dots, close to N78A. Fully opened, lower surface: Close to 77B; towards the base, close to 77C; at the base, tinged with close to 196A; venation, close to N78B.

*Peduncles*.—Length: About 58.3 cm. Diameter: About 5 mm. Strength: Strong. Aspect: Upright to outwardly arching. Texture and luster: Smooth, glabrous; matte. Color: Close to 147A moderately covered with fine dots, close to 147D.

*Pedicels*.—Length: About 3.5 cm. Diameter: About 3 mm. Strength: Moderately strong. Aspect: About 60° from peduncle axis. Texture and luster: Smooth, glabrous; matte. Color: Close to 177C; distal end, close to 75B; proximal end, close to N199B.

*Reproductive organs*.—Androecium: Column length: About 9 mm. Column width: About 6 mm. Column color: Close to N75C; distally, close to N155A. Pollinia quantity: Two. Pollinia diameter (per two pollinia): About 2.5 mm. Pollinia color: Close to 24A. Gynoecium: Stigma length: About 3 mm. Stigma width: About 4.5 mm. Stigma shape: Reniform. Stigma color: Close to N155A. Ovary length: About 1 cm. Ovary diameter: About 1 mm. Ovary color: Close to 149B. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'Bombshell' as herein illustrated and described.

* * * * *